United States Patent [19]

Carr et al.

[11] Patent Number: 5,183,690

[45] Date of Patent: Feb. 2, 1993

[54] STARCH ENCAPSULATION OF BIOLOGICALLY ACTIVE AGENTS BY A CONTINUOUS PROCESS

[75] Inventors: Merle E. Carr, Chillicothe; William M. Doane, Morton; Robert E. Wing, Peoria; Edward B. Bagley, Morton, all of Ill.

[73] Assignee: The United States of America, as represented by the Secretary of Agriculture, Washington, D.C.

[21] Appl. No.: 542,566

[22] Filed: Jun. 25, 1990

[51] Int. Cl.$^5$ .................. B01J 13/04; A29C 47/00; A61K 9/62; A61K 9/16

[52] U.S. Cl. .................. 427/213.31; 427/213.3; 264/4.1; 264/4.6; 264/204; 264/211.11; 264/211.12; 426/96; 424/493; 424/499

[58] Field of Search .......... 264/4.1, 4.3, 4.6, 204, 264/211.11, 211.12; 427/213.3, 213.31; 428/402.2, 402.24; 426/96

[56] References Cited

U.S. PATENT DOCUMENTS

| | | | |
|---|---|---|---|
| 2,876,160 | 3/1959 | Schoch et al. | 167/82 |
| 3,159,585 | 12/1984 | Evans et al. | 264/4.6 X |
| 3,499,962 | 3/1970 | Wurzburg et al. | 264/4.6 X |
| 3,666,557 | 5/1972 | Jensen et al. | 127/32 |
| 3,786,123 | 1/1974 | Katzen | 264/4.7 X |
| 3,922,354 | 11/1975 | Galluzzi et al. | 426/96 |
| 3,971,852 | 7/1976 | Brenner et al. | 264/4.6 X |
| 4,230,687 | 10/1980 | Sair et al. | 424/22 |
| 4,755,397 | 7/1988 | Eden et al. | 427/213.3 |
| 4,812,445 | 3/1989 | Eden et al. | 514/60 |
| 4,859,377 | 8/1989 | Shasha et al. | 264/4.1 |
| 4,911,952 | 3/1990 | Doane et al. | 427/213.31 |

FOREIGN PATENT DOCUMENTS

WO85/04074  9/1985  PCT Int'l Appl.

*Primary Examiner*—Robert L. Stoll
*Assistant Examiner*—John M. Covert
*Attorney, Agent, or Firm*—M. Howard Silverstein; Curtis P. Ribando; John D. Fado

[57] ABSTRACT

Biologically active agents to be encapsulated are continuously blended with a starchy material and water, subjected to high-shear mechanical action at a temperature above the gelatinization temperature of starch, and continuously recovered as an insolubilized matrix of starch that entraps discontinuous domains of the agent. Alternatively, the core material to be encapsulated is added and blended with the aqueous dispersion of starch after the starch and water have been subjected to an elevated temperature sufficient to gelatinize the starch. Rate of release of agents to the environment can be controlled by preselecting a set of conditions related to various processing parameters. Encapsulation of biologically active compositons provides protection against degradative environmental conditions, improves safety in handling, and slows the release of such compounds to the surrounding medium.

7 Claims, No Drawings

STARCH ENCAPSULATION OF BIOLOGICALLY ACTIVE AGENTS BY A CONTINUOUS PROCESS

BACKGROUND OF THE INVENTION

1. Field of the Invention

This invention relates to a continuous process for encapsulating agricultural chemicals, biopesticides, food constituents, medicaments, and other biologically active agents for controlling their release and protecting them from degradation due to environmental exposure and to the compositions prepared thereby.

2. Description of the Prior Art

Various approaches to the controlled release of chemical biological active agents by means of a starch-based encapsulating material have been disclosed previously. Some of these methods have involved the use of chemical crosslinking reactions. In U.S. Pat. No. 4,382,813, Shasha discloses a system for encapsulating certain types of pesticidal agents by the rapid insolubilization of a starch-containing material alkoxide with a bivalent cation selected from the group of calcium, barium, and strontium. While this system is applicable to water-insoluble agents, it is not particularly suitable for those which are water soluble, nor for substances susceptible to alkali degradation.

In U.S. Pat. No. 4,439,488, Trimnell et al. disclose a method of encapsulation wherein entrapment is achieved by insolubilization of a polyhydroxy polymer with boric acid or a boric acid derivative at a mildly alkaline pH. This system is applicable to a broader spectrum of active agents than that of Shasha, supra, but is not suitable for products intended for human ingestion.

Controlled release by means of starch-based encapsulating materials can also be accomplished without the use of chemical crosslinking reactions. In U.S. Pat. No. 2,876,160, Schoch et al. disclose such a method which employs modified, amylose-free starches at concentrations up to 65% solids for embedding water-insoluble materials.

In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4,230,687, Sair et al. disclose the application of shearing stress, vigorous mechanical working, and heat to distribute active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solids matrices prepared from partially gelatinized unmodified starches. Additives such as modified dextrins, mixtures of mono- and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 min followed by passage through a homogenizer to effect disruption of granules without degradation of molecules.

Shasha et al. (U.S. Pat. No. 4,859,377) teach the use of amylose-containing pregelatinized starch to encapsulate entomopathogens, thereby protecting such biocontrol agents from environmental degradation and also promoting infection of target pests. The encapsulation is effected in an aqueous dispersion of the pregelatinized starch: for dry, granular products, the starch solids content of the dispersion is 25–40%; for sprayable liquid products, chemically degraded starch is used at a solids content of 1–10%.

Doane et al. (U.S. Pat. No. 4,911,952) disclose a method for the encapsulation of chemical biological agents using aqueous dispersions of amylose-containing unmodified starch wherein the starch solids content is 20–40% and starch dispersion is accomplished by high-temperature cooking.

SUMMARY OF THE INVENTION

We have now unexpectedly discovered that when biologically active agents are encapsulated in a matrix of starchy material in an extrusion process, an array of processing parameters can be defined for controlling the release properties of the active agent from the matrix of starchy material. The process essentially comprises:

a. establishing an array of the processing parameters;
b. preselecting a set of conditions defined by the parameters, which set of conditions will yield the predetermined release properties;
c. continuously blending the starchy material, the active agent, and water in an ingredient stream;
d. continuously extruding said ingredient stream as an extrudate; and
e. continuously recovering the extrudate;

wherein the conditions of blending, extruding, and recovering comprise said set of conditions whereby the extrudate is an encapsulated biologically active agent having the predetermined release properties.

In accordance with this discovery, it is an object of the invention to provide a facile, universal, and industrially acceptable method for encapsulation of core materials whereby the properties of the encapsulated products are readily controllable.

It is also an object of the invention that the primary matrix-forming material be derived from natural renewable resources.

Another object of the invention is that the primary matrix-forming material be safe for human ingestion.

It is a further object of the invention to provide a novel free-flowing particulate product in which discontinuous domains of biologically active core materials are entrapped by a continuous matrix of starchy material.

Another object of the invention is to provide a product in which the encapsulated substance is sufficiently protected to be safe for handling, controllably released to a wide variety of environments, and resistant to losses by volatilization, leaching, wind transport, air oxidation, digestion, and sunlight decomposition.

Other objects and advantages of this invention will become readily apparent from the ensuing description.

DETAILED DESCRIPTION OF THE INVENTION

The array of processing parameters contemplated herein as having an effect on the release properties of the biologically active agents encapsulated in the matrix of starchy material includes, but is not limited to, the following: the solids concentration in the ingredient stream; the extrusion temperature; the configuration of the exit die; the moisture content of the dried extrudate prior to grinding, and the mesh size of the ground particles. In the ensuing discussion and examples, a description of the range of conditions related to each of these parameters and the effects of those conditions on release properties is presented. By predetermining the effects of one or more of those conditions on the release properties, a set of conditions can be preselected by a person in the art to achieve a product having a particular rate of release.

The starting encapsulating material contemplated for use in the invention includes unmodified natural granular starches such as regular, waxy, and high amylose cereal, potato, and tapioca starch, and flours containing the same, as well as mixtures of these starches and flours. Full-fat starches, that is, starches which have not had a portion of the bound fat removed, are suitable for use herein.

Biologically active agents which are suitable for use herein may be any organic or inorganic solids capable of being finely divided, or any liquid, or any biological material, provided that the agent does not interfere with the encapsulating process, and does not react with or dissolve the encapsulating matrix. Particularly envisioned are biocontrol agents, chemicals and chemical biological formulations which meet the above criteria and which are classified as a known herbicide, insecticide, fungicide, nematocide, bactericide, rodenticide, molluscicide, acaricide, larvacide, fumigant, animal repellant, plant growth regulator, fertilizer, pheromone, flavor composition, odor composition, vitamin, mineral, or medicament.

Other compositions suitable as core materials for use in accordance with the invention will be known to those skilled in the art. Core materials dissolved, emulsified, or otherwise dispersed in solvents or carriers, as well as compatible combinations of the above types of compositions are also easily encapsulated by the instant method.

The core material to be encapsulated is blended with the starch and subjected to high-shear mechanical action under conditions that result in substantially uniform distribution of the core material throughout the starch. Water should be present in an amount sufficient to achieve a starch solids concentration of up to about 70%. To realize the advantages of the invention in terms of a practical, continuous operation for encapsulation, the minimum starch solids concentration should be at least 40%. The temperature is elevated to at least about 65° C. to effect gelatinization of starch and assure an essentially molecular dispersion of the starch in the water. Alternately, the core material to be encapsulated is added and blended with the aqueous dispersion of starch after the starch and water have been subjected to an elevated temperature sufficient to gelatinize the starch. In this embodiment the aqueous starch stream containing gelatinized starch may be lowered to a temperature as low as about 25° C. before the core material to be encapsulated is added and subjected to high-shear mechanical action (Example 66). Under such low temperature conditions of admixture, the activity of sensitive biological material, such as bacteria and viruses, is preserved; and loss of volatile organic materials is minimized. Use of an extruder in accordance with the preferred embodiment of the invention provides the requisite heat, mixing, compounding, high-shear mechanical action and continuous processing.

For purposes of this invention, the starch dispersion is considered to be in the aqueous phase, which will constitute the continuous phase of the encapsulation system. This system is effective to achieve encapsulation without the presence of any additional encapsulating agent.

The domains of the agent, which constitute the discontinuous phase of the mixture, should be sufficiently small to be entrapped by the continuous phase. It would be within the skill of a person in the art to determine the maximum level at which a particular agent can be effectively loaded into the system. However, based on Example 9–12, it is clear that as much as 20% active ingredient by weight can be incorporated with 86–89% encapsulation. For purposes of performance, effective amounts of core materials depend entirely on the type and characteristics of the core material, on matrix thickness, and on the intended utility of the product. A very volatile liquid, for instance, would require a thicker structure than a nonvolatile solid, and accordingly should be incorporated at a lower level. Similarly, a volatile liquid to be completely withheld from the environment would be incorporated at a lower level than one to be used as a slow-release pesticide. The expression "an effective amount" in reference to the active agent is defined herein as that amount of core material which will achieve the desired result (e.g., attract, repel, or kill pests; release a detectable aroma, flavor, nutrient, or pharmaceutically active dosage of medicament; or enhance the growth of plants) when the encapsulated composition containing the effective amount of the agent is placed in the proper environment.

Encapsulation of the biologically active agent into the starch matrix is initiated by uniformly dispersing the agent throughout an aqueous dispersion of the gelatinized starch. The order of combining the various components of the formulation is not critical and may be conducted in whatever manner best facilitates the process. Under suitable gelation conditions, the starch which has been dispersed in an aqueous medium begins to retrograde, thereby forming a gelatinous mass. By proper formulation as described in more detail below, the dispersion will gel and can thereafter be taken to dryness. The reassociation of the amylose components of the starch results in a substantially homogeneous mass analagous to the precursive mixture in which, now, discontinuous domains of active ingredient are uniformly dispersed throughout a continuous starch matrix. This process distinguishes from microencapsulation which yields discrete particles, each comprising a domain of agent enveloped by a film or coating of encapsulating agent. In accordance with one method of recovery, the extruded mass is either pelletized and dried to about 10% moisture or dried first to about 10% moisture and thereafter ground to a desired particle size.

As shown in the examples, the invention process achieves high levels (up to 99%) of encapsulation of active agent. We have surprisingly found that the level of encapsulation is improved by dry-grinding the friable agent-containing starch matrix (Examples 35–38, Table IV). This finding is completely contrary to the teaching of Stout et al. [J. Appl. Polym. Sci. 24: 158 (1979)], who theorized that dry-grinding effected irreversible rupturing of capsules accompanied by evaporative loss of active agent.

The rate of swelling of the products in water and the rate of release of active agent are controlled simply and conveniently over a wide range, without the use of chemical treatments or additional processing, by altering the amount of water present in the starch-agent-water blend during processing. As the amount of water is decreased (and starch concentration is increased), both the swelling rate and the release rate increase (Examples 1-5, Table I). This phenomenon is completely unexpected in view of teachings of the prior art (Doane et al., supra) which indicate that the reverse is true when the granules of the encapsulating starch have been disrupted by means of steam-injection cooking. The rate of swelling of the products in water and the rate of release of active agent also are controlled simply and conveniently over a wide range by passage of the extrudate containing starch-agent-water through an exit die of various dimensions. As the exit die is reduced in size, both the rate and extent of swelling increase and the rate of release of agent increases (Examples 26–31, Table III). The most desirable concentration of starch in this invention is considered to be within the range of about 40–75%, a higher range than those possible in the prior art. The following examples are intended only to further illustrate the invention and are not intended to limit the scope of the invention which is defined by the claims.

All percents herein disclosed are "by weight" unless otherwise specified.

EXAMPLES 1–5

Effect of Starch Concentration

Encapsulation was performed in a 30-mm, corotating, intermeshing, twin-screw extruder with a 15-HP, DC drive and screw speeds from 50–500 RPM. The processing portion consisted of 14 barrel sections (each 90 mm long), one barrel spacer (30 mm long), and an end plate (30 mm long), coupled by 4 tie rods. Barrel bore and screw diameters were 30.85 and 30.70 mm, respectively. Each barrel section, except the first, had an electric heater (500 watts). Barrel temperature thermocouples were located at sections 3, 5, 7, 9, 11, 12, and 14 (7 zones). Thermocouples for measuring material temperature were located at section 9 and at the die head, which was equipped with a 1500-watt heater. Chilled water was circulated through the barrel section jackets, which were equipped with solenoid valves and return line check valves to regulate barrel temperatures. The twin screw comprised 67 individual slip-on elements of various types on each shaft for feeding, conveying, mixing, and extruding the materials under various conditions of concentration, temperature, pressure, speed, and shear. The last barrel section (14) was equipped with a die-head assembly that permitted optional use of a die. All processing conditions were controlled and monitored from a remote instrument panel.

The granular herbicide atrazine (1.17 lb) was blended with pearl corn starch (22.2 lb, 10% moisture). The blend, containing 5% atrazine, was fed by a twin-screw feeder into barrel section 1 of the extruder at the rate of 88.4 g/min (75.60 g dry starch, 8.40 g moisture, 4.42 g atrazine), and water was fed by a high-pressure piston displacement pump into barrel section 3 at rates ranging from 24.0 ml/min, giving a starch concentration of 70% (dry starch/as-is starch plus water added) to 132 ml/min (35% starch). The resulting starch concentrations are listed in Table I. Barrel section temperatures were set at 70° C. in section 3; 90° C. in 5; 100° C. in 7, 9, and 11; and 90° C. in 12, 14, and the die head. Screw speed was 400 RPM, and no die was used. Extruded materials were air-dried to about 10% moisture, milled, and sieved to 20–40 mesh granular products. Each product was washed with chloroform and quantitatively analyzed for entrapped (encapsulated) atrazine, for degree of swelling in water after submersion for 24 hr, and for percentage of herbicide released into aqueous ethanol (10% ethanol by volume) in 24 hr. The results in Table I show that encapsulation efficiency was high in all the examples, that a wide range of release rates were obtained, and that both water swelling and agent release surprisingly increased with starch concentration.

EXAMPLES 6–7

Encapsulation of 15% Atrazine

The procedures of Examples 1 and 4 were repeated except that the concentration of atrazine was 15% instead of 5%. Both encapsulated products contained 80% of the agent initially added. The product processed at 35% starch concentration (Example 6) swelled 220% in water, and that processed at 65% starch (Example 7) swelled 260%.

EXAMPLE 8

Effect of Larger Particles

The procedures of Example 5 were repeated except that the dry, milled extrudate was sieved to obtain a 10–20 mesh product. The product encapsulated also 97% of the agent initially added.

EXAMPLES 9–12

Encapsulation of 20% Atrazine

The procedures of Examples 1–4 were repeated except that the concentration of atrazine was 20% instead of 5%, and the dry, milled extrudate was sieved to obtain a 10–20 mesh product. The products encapsulated 86–89% of the agent initially added.

EXAMPLES 13–16

Encapsulation of 10% Atrazine

The procedures of Examples 1–4 were repeated except that the concentration of atrazine was 10% instead of 5%. The products encapsulated 84–90% of the agent initially added.

EXAMPLES 17–20

Effect of Barrel Temperature

The procedures of Example 1 were repeated except that all barrel section temperatures were set successively at the temperatures listed in Table II.

EXAMPLE 21

Encapsulation of a Liquid Agent, Metolachlor

The procedures of Example 1 were repeated except that starch alone (10% moisture) was fed into barrel section 1 at the rate of 84 g/min, water was fed into section 2 at the rate of 132 ml/min (35% starch concentration), and the liquid herbicide metolachlor was fed into section 3 at the rate of 9.3 g/min of active agent (10% concentration in the encapsulated product). The product encapsulated 89% of the initial agent, swelled 160% in water in 24 hr, and released 90% of the agent in 21 hr. in distilled water.

EXAMPLE 22

Metolachlor with Higher Starch Concentration

The procedures of Example 21 were repeated except that the water feed rate was 32.3 ml/min (65% starch). The product encapsulated 69% of the initial agent, swelled 180% in water, and released 100% of the agent.

EXAMPLES 23-24

Liquid Agent with Surfactant

The procedures of Examples 21 and 22 were repeated except that the liquid herbicide "Dual", which contains a surfactant, was substituted for metolachlor. The product that had been processed with 35% starch (Example 23) encapsulated 90% of the initial agent, swelled 150% in water, and released 95% of the agent. The product processed with 65% starch (Example 24) encapsulated 83% of the initial agent, swelled 190% in water, and released 97% of the agent.

EXAMPLE 25

Low-Melting Solid Agent

The procedures of Example 21 were repeated except that alachlor was substituted for metolachlor. Alachlor is a crystalline herbicide that liquifies at 40° C.; it was pumped into the extruder at 50° C. as a melt. The product encapsulated 83% of the initial agent, swelled 200% in water, and released 47% of the agent.

EXAMPLES 26-27

Extrusion through a Die

The procedures of Example 22 were repeated except that the screw speed was 200 RPM (Example 26) instead of 400 RPM. This procedure was then repeated using a die with 2, 4-mm-diameter holes (Example 27). Product characteristics are given in Table III.

EXAMPLES 28-29

The procedures of Examples 26 and 27 were repeated except that the water feed rate was 24.0 ml/min (70% starch), the screw speed was 400 RPM, and the die had 4, 2-mm-diameter-holes. The operation without the die was Example 28; that with the die, Example 29. Product characteristics are given in Table III.

EXAMPLES 30-31

The procedures of Examples 26 and 27 were repeated except that "Dual" (supra) was substituted for metolachlor, and the screw speed was 400 RPM. The operation without the die was Example 30; that with the die, Example 31. Product characteristics are given in Table III.

EXAMPLES 32-33

Waxy and High-Amylose Starches

The procedures of Example 4 were repeated except that waxy corn starch (Example 32) and 70%-amylose corn starch ("Amylon VII" starch, Example 33) were substituted for pearl corn starch. The products encapsulated 75% and 91% of the agent, respectively.

EXAMPLE 34

Two-Part Addition of Starch

The procedures of Example 1 were repeated with the following exceptions: Additional starch alone was fed into section 11 to increase the starch concentration from 35% to 65% and to result in an agent concentration of 2.5% when the product was dried to 10% moisture; and barrel section temperatures were changed to 50° C. in section 11 and to 70° C. in section 12. The product encapsulated 99% of the agent and swelled 580% in water. Both of these values are higher than those of Examples 1-5 (Table I).

EXAMPLES 35 AND 36

Effect of Dry Grinding; Large-Scale Encapsulation

Encapsulation was performed in a 57-mm twin-screw extruder of the same type and design as in Example 1, but with 10 barrel sections instead of 14. Starch was fed into barrel section 1 at the rate of 150 lb/hr (135 lb/hr, dry); deionized water was fed into section 2 at the rate of 42.9 lb/hr to give a starch concentration of 70%; and "Dual" liquid herbicide was fed into section 4 to give 10% herbicide in the extrudate after drying to 10% moisture. The die-head assembly was equipped with a die having twenty 5-mm-diameter holes and a pelletizer. Screw speed was 200 RPM. Barrel temperatures were 75° C. at sections 2-4 and 95° C. at sections 5-10. Section 1 was water cooled. The pelletized extrudate was air dried, milled, sieved (14-20 mesh), and analyzed as in Example 1. One product (Example 35) was initially dried to 25% moisture before milling, sieving, and further drying to about 10% moisture; another product (Example 36) was dried to 7% moisture before milling, sieving (14-20 mesh), and analysis. The results in Table IV show that, in contrast to teachings of the prior art (Stout et al., supra), dry grinding resulted in more complete encapsulation of agent.

EXAMPLES 37 AND 38

The procedures of Examples 35 and 36 were repeated except that alachlor (supra) was substituted for "Dual". One product (Example 37) was initially dried to 16.5% moisture before milling, sieving (14-20 mesh), and further drying to about 10% moisture; another product (Example 38) was dried to 2.3% moisture before milling, sieving (14-20 mesh) and analysis. The results in Table IV are similar to those of Examples 35 and 36.

EXAMPLES 39-50

Encapsulation of a Volatile Liquid Agent, "EPTC+R29148"

The procedures of Examples 21 and 22 were repeated except that an intermediate water feed rate was added, the liquid herbicide "EPTC+R29148" was substituted for metolachlor, herbicide feed rate was 15 g/min of active agent (15% concentration in the encapsulated product), and granular products were obtained at 14-20 mesh as well as 20-40 mesh. Product characteristics are given in Table V. The products were also oven-dried at 50° C. for 24 hr.; the resulting characteristics are given in Table VI.

EXAMPLE 51

Encapsulation of Atrazine-Alachlor (Ratio 3:5)

Combined procedures of Examples 4 and 22 were repeated except that the initial starch-agent blend contained 6% atrazine instead of 5% (Example 4); and alachlor was substituted for metolachlor (Example 22). The product (14-20 mesh) encapsulated 95% of the initial agents and swelled 340% in water.

EXAMPLE 52

Encapsulation of a Volatile Food Additive

The procedures of Example 22 were repeated except that orange oil (D-limonene) was substituted for metolachlor, and it was fed at the rate of 11.9 ml/min. The product encapsulated 84% of the initial agent and swelled 200% in water.

EXAMPLES 53-56

Encapsulation of Atrazine in Corn Flour

The procedures of Examples 1 and 4 were repeated except atrazine (5%) was preblended with corn flour. Product characteristics are given in Table VII.

EXAMPLES 57-64

Encapsulation of Metolachlor and "Dual" in Corn Flour

The procedures of Examples 1 and 4 were repeated except metolachlor or "Dual" (10%) were metered in barrel section 7 into the gelatinized corn flour. Product characteristics are given in Table VIII.

EXAMPLE 65

Encapsulation of an Entomopathogen in Cornstarch

The procedures of Examples 1-5 were used with the following exceptions: Starch (9 lb. with 10% moisture) was preblended with 0.2 lb. of the entomopathogen (a commercial *Bacillus thuringiensis* product) and 1 lb. of an insect feeding ingredient ("Coax") and fed into the extruder at the rate of 93 g./min. Water was fed into the extruder at the rate of 76 ml./min. Screw speed was 200 rpm; all barrel temperatures were 65° C.; and the die head heater was 65° C. The product was extruded through a die with two 4-mm-diameter holes. The extruded product, 16-40 mesh, exhibited excellent biological activity.

EXAMPLE 66

The procedures of Example 1 were used with the following exceptions and clarifications: Starch alone at 10% moisture was fed into the first barrel section; water was fed into the third barrel section; and atrazine (5%) was fed into barrel section 11. Starch concentration was 35%. Barrel temperatures were 50° C. at section 11 and 30° C. at sections 12, 13, and 14 and at the die head assembly. Encapsulation efficiency was 94% for a 10-20 mesh product and 95% for a 20-40 mesh product. The latter product swelled 180% in distilled water (24 hr.).

EXAMPLE 67

Encapsulation of "EPTC+R29148" Adsorbed onto Silica Gel

The procedures of Example 21 were followed except the water feed rate was 100 ml./min. (45% starch concentration) into barrel section 2 and a preblend of "EPTC+R29148" (40%) and silica gel (60-100 mesh, 60%) was fed into barrel section 7 at a rate of 130 g./min. The products encapsulated at least 90% of the active agent.

It is understood that the foregoing detailed description is given merely by way of illustration and that modification and variations may be made therein without departing from the spirit and scope of the invention.

TABLE I

| Example | % Starch | % Swelling | % Agent released | % Agent encapsulated |
|---|---|---|---|---|
| 1 | 35 | 160 | 23 | 96 |
| 2 | 45 | 180 | 25 | 92 |
| 3 | 55 | 200 | 27 | 94 |
| 4 | 65 | 260 | 33 | 90 |
| 5 | 70 | 380 | 47 | 90 |

TABLE II

| Example | Barrel temp. (°C.) | % Agent encapsulated |
|---|---|---|
| 17 | 58 | 12 |
| 18 | 68 | 85 |
| 19 | 78 | 94 |
| 20 | 98 | 96 |

TABLE III

| Example | % Starch | Agent | Die | Swelling[a] | % Agent Released[a] |
|---|---|---|---|---|---|
| 26 | 65 | Metolachlor | None | 240 | 84 |
| 27 | 65 | Metolachlor | 2, 4-mm holes | 360 | 92 |
| 28 | 70 | Metolachlor | None | 360 | 96 |
| 29 | 70 | Metolachlor | 4, 2-mm holes | 500 | 100 |
| 30 | 65 | "Dual" | None | 280 | 80 |
| 31 | 65 | "Dual" | 4-mm holes | 420 | 94 |

[a] Values determined after 24 hrs.

TABLE IV

| Example | Agent | % Moisture at Grinding | % Agent Encapsulated |
|---|---|---|---|
| 35 | "Dual" | 25.0 | 50 |
| 36 | "Dual" | 7.0 | 77 |
| 37 | Alachlor | 16.5 | 80 |
| 38 | Alachlor | 2.3 | 95 |

TABLE V

| Example | % Starch | Mesh Size | % Agent Encapsulated | % Swelling |
|---|---|---|---|---|
| 39 | 35 | 14-20 | 100 | 180 |
| 40 | 35 | 20-40 | 97 | 200 |
| 41 | 50 | 14-20 | 85 | 200 |
| 42 | 50 | 20-40 | 61 | 220 |
| 43 | 65 | 14-20 | 79 | 280 |
| 44 | 65 | 20-40 | 69 | 300 |

TABLE VI

| Example | % Starch | Mesh Size | % Agent Encapsulated | % Swelling |
|---|---|---|---|---|
| 45 | 35 | 14-20 | 97 | 220 |
| 46 | 35 | 20-40 | 87 | 240 |
| 47 | 50 | 14-20 | 94 | 260 |
| 48 | 50 | 20-40 | 74 | 280 |
| 49 | 65 | 14-20 | 83 | 320 |

TABLE VI-continued

| Example | % Starch | Mesh Size | % Agent Encapsulated | % Swelling |
|---|---|---|---|---|
| 50 | 65 | 20-40 | 59 | 340 |

TABLE VII

| Example | % Corn Flour | Mesh Size | % Agent Encapsulated | % Swelling |
|---|---|---|---|---|
| 53 | 35 | 14-20 | 94 | — |
| 54 | 35 | 20-40 | 90 | 190 |
| 55 | 65 | 14-20 | 99 | — |
| 56 | 65 | 20-40 | 80 | 240 |

TABLE VIII

| Example | % Corn Flour | Active Agent | Mesh Size | % Agent Encapsulated | % Swelling |
|---|---|---|---|---|---|
| 57 | 35 | Metalachlor | 10-20 | 88 | — |
| 58 | 35 | Metalachlor | 20-40 | 77 | 160 |
| 59 | 35 | "Dual" | 10-20 | 88 | — |
| 60 | 35 | "Dual" | 20-40 | 79 | 170 |
| 61 | 65 | Metalachlor | 10-20 | 76 | — |
| 62 | 65 | Metalachlor | 20-40 | 62 | 160 |
| 63 | 65 | "Dual" | 10-20 | 77 | — |
| 64 | 65 | "Dual" | 20-40 | 63 | 160 |

We claim:

1. A continuous process for imparting predetermined release properties to an encapsulated biologically active agent in a matrix of starchy material comprising the steps:

a. establishing an array of processing parameters in a process for producing said encapsulated biologically active agent by extrusion, which parameters have an effect on the release properties of the active agent from the matrix of starchy material;

b. preselecting a set of conditions defined by the parameters, which set of conditions will yield the predetermined release properties;

c. continuously blending the starchy material, the active agent, and water in an ingredient stream, wherein the starchy material is at a solids concentration of at least 40% and comprises an unmodified regular or waxy cereal, potato, or tapioca starch or a flour containing said starch, or a mixture of these starches or flours;

d. continuously extruding said ingredient stream as an extrudate; and e. continuously recovering the extrudate;

wherein the conditions of blending, extruding, and recovering comprise said set of conditions whereby the extrudate is an encapsulated biologically active agent having the predetermined release properties.

2. The method as described in claim 1, wherein said starchy material is pregelatinized starch.

3. The method as described in claim 1, wherein said starchy material is selected from the group consisting of pearl corn starch, corn flour, wheat starch, wheat flour, potato starch, potato flour, waxy starch, and mixtures thereof.

4. The method as described in claim 1, wherein one of the parameters is solids concentration in said ingredient stream.

5. The method as described in claim 1, wherein the ingredient stream is passed through an exit die to yield the extrudate and one of the parameters relates to the configuration of the exit die.

6. The method as described in claim 1, wherein the extrudate is recovered by drying the mixture to a predetermined moisture content and particularizing the dried extrudate into discrete particles, and two of the parameters relate to the moisture content of the dried extrudate and mesh size of the particles.

7. The method as described in claim 1, wherein one of the parameters relates to the extrusion temperature.

* * * * *